United States Patent [19]

Huvé

[11] 4,416,885
[45] * Nov. 22, 1983

[54] USE OF ISOPROPYLAMINOPYRIMIDINE IN THE CHEMOTHERAPY OF MUSCULAR DYSTROPHY, MYOPATHY AND MYOTONIA

[76] Inventor: Pierre M. Huvé, 3, rue Cernushi, 75017 Paris, France

[*] Notice: The portion of the term of this patent subsequent to Aug. 17, 1999 has been disclaimed.

[21] Appl. No.: 360,497

[22] Filed: Mar. 22, 1982

Related U.S. Application Data

[63] Continuation-in-part of Ser. No. 201,709, Oct. 29, 1980, Pat. No. 4,344,947.

[51] Int. Cl.³ .............................................. A61K 31/505
[52] U.S. Cl. ..................................................... 424/251
[58] Field of Search ......................................... 424/251

[56] References Cited

U.S. PATENT DOCUMENTS 4,073,895  2/1978  Esanu ................................. 424/200

*Primary Examiner*—Stanley J. Friedman
*Attorney, Agent, or Firm*—Thompson, Birch, Gauthier & Samuels

[57] ABSTRACT

A method for the chemotherapy of muscular dystrophy which includes administrating orally an effective amount of 2 isopropylaminopyrimidine.

5 Claims, 10 Drawing Figures

USE OF ISOPROPYLAMINOPYRIMIDINE IN THE CHEMOTHERAPY OF MUSCULAR DYSTROPHY, MYOPATHY AND MYOTONIA

CROSS-REFERENCE TO RELATED APPLICATION

This application is a continuation-in-part application of U.S. Ser. No. 201,709, filed Oct. 29, 1980, U.S. Pat. No. 4,344,947.

BACKGROUND AND BRIEF SUMMARY OF THE INVENTION

The present invention is directed to a new use of an existing compound. U.S. Pat. No. 4,073,895 relates to the use of a substituted salt of 2-aminopyrimidine. This patent in fact teaches that a particular salt of 2-aminopyrimidine, namely 2-isopropylaminopyrimidine orthophosphate (IAPP), is useful as an active agent for the treatment of neuropathies. Although this use is known, the particular efficacy of the salt against muscular dystrophy has yielded encouraging results.

The invention broadly comprises a method for the chemotherapy of muscular dystrophy, which comprises administering either orally or by injection or administering by any method known to those skilled in the art an effective dosage of 2-isopropylaminopyrimidine or therapeutically acceptable salts of the same or the hydroxylated and oxygenated metabolites thereof.

DESCRIPTION OF THE PREFERRED EMBODIMENT

In the following discussion, the specific compound used for testing is 2 isopropylaminopyrimidine orthophosphate as disclosed in U.S. Pat. No. 4,073,895, which patent is hereby incorporated by reference in its entirety in this application.

EXAMPLE I

The dystrophic chicken homozygote was used for monitoring chemotherapy of muscular dystrophy. This particular animal line inherits dystrophy in a form as close as possible in causation and course to human dystrophy and also permits quantitative assessment of progress of the disease by several independent methods.

The compound IAPP was tested on dystrophic New Hampshire chickens, line 413, and Imperial College (London, England) sub-line of the original Davis, University of California strain. The chickens are homozygous for muscular dystrophy, the disease appearing with 100% incidence.

Chemotherapy was assessed by application of seven different parameters: physical tests of muscular disability, namely the flip test and wing apposition (W.A.) measurements; biochemical assays of serum and muscle enzume levels of creatine phosphokinase (CPK), pyruvate kinase (PK) and acetylcholinesterase (AChE); and histological comparisons of treated and untreated muscle. Toxicity studies (weight loss, etc.) were also used. A very comprehensive profile of the drug was thus obtained which related to all the known, highly characteristic features of the disease which are applicable to both the animal model and the human.

DESCRIPTION OF TESTS

1. The Flip Test

The animal is placed on its *back* in the supine position. The number of times it is able to rise, out of five attempts, is known as the flip number (FN). The normal chicken invariably scores 5 (out of 5 attempts), whereas in an untreated dystrophic chicken, the number declines to zero in 6-8 weeks. The test is performed once every day, seven days; more frequent assessment introduces an exercise factor and is not recommended.

2. Wing Apposition Measurements

This can be defined as the minimum separation in cm to which the two wing tips can be passively raised, providing a measure of the characteristic loss is flexibility of the wing muscle-tendon system. The test is performed once weekly. In dystrophic birds, WA changes after the first three weeks of life from 0 cm (wings raised and touching) to about 18 cm at 3 months (wings stiff and can barely be raised). The normal controls maintain a score of 0 cm throughout.

3. Plasma CPK

Plasma CPK rises dramatically in the dystrophic chicken as it does also in the human disease. The normal chicken has 200-300 U/l CPK, compared to about 20,000 U/l in the untreated dystrophic chicken at its peak. It rises to these high levels over a period of two months and is, therefore, a significant index of the disease.

4. Plasma PK

A massive rise in this enzyme level also occurs in the dystrophic chicken compared to the normal control, as it does in the human disease.

5. Plasma AChE

The elevation of this enzyme in the dystrophic chicken occurs from 8 days and reaches a plateau at 100 days, compared to the normal animal where the levels continue to decline slowly.

6. Histopathology

Muscle fibre area increase greatly in the dystrophic chicken as does the range of fibre area sizes. Nuclei become displaced peripherally and both features can be measured quantitatively and compared with normal controls.

7. Forms of AChE in the Muscle

Toxicity

Weight measurements are taken weekly, weight loss, diarrhea or any other symptoms are noted. No drugs have yet been described for dystrophy with a beneficial effect without an accompanying weight loss.

The drug was administered daily in water, injected intra-peritoneally, the amount being adjusted on a weekly basis according to the animal's weight.

Median Lethal Dose

Initial single injections of IAPP at 50 mg/Kg and 100 mg/Kg produced no weight loss over 7 days, nor any other toxic symptoms.

| Experiment No. 1 | |
| --- | --- |
| Dosage | 30 mg/Kg |
| No. Treated Animals | 8 |
| No. Control Animals | 7 |

| Experiment No. 2 | |
| --- | --- |
| Dosage | 40 mg/Kg |
| No. Treated Animals | 7 |
| No. Control Animals | 7 |

| Experiment No. 3 | |
| --- | --- |
| Dosage | 70 mg/Kg |
| No. Treated Animals | 10 |
| No. Control Animals | 10 |

Experiment No. 1

Dosage at 30 mg/Kg IAPP showed no significant differents between the treated and dystrophic control animals in the parameters measured.

Experiment No. 2

Results of dosage at 40 mg/Kg IAPP are set forth below in Table I. The results showed a significant effect of IAPP on all parameters measured. CPK, PK and AChE enzyme levels were reduced dramatically, although the effect was declining at the end of the 10-week experiment. The Flip number and wing apposition measurements gave a valuable measure of the bird's immediate physical condition, and showed a significant improvement in the treated group.

Experiment No. 3

Results of dosage at 70 mg/Kg IAPP are set forth below in Table 2. The results after 4 weeks treatment showed a similar effect to treatment at 40 mg/Kg at this stage. Both experiments appear to show that the drug is effective at an early age. The higher dosage also produces detectable toxicity as evidenced by weight loss, but this is still moderate.

Significant effects are reached on the parameters measured with little or no concomitant toxic effects.

TABLE I

| | | | EXPERIMENT 2 - IAPP - 40 mg/Kg | | | | | |
| --- | --- | --- | --- | --- | --- | --- | --- | --- |
| Day | *% Weight Change | % CPK Change | % PK Change | % AChE Change | FN Treated | FN Control | WA Treated | WA Control |
| 7-13 | -0.04 | -8 | | | 4.9 | 4.5 | 0 | 0 |
| 14-20 | -0.07 | -46 | -38 | | 5.0 | 4.8 | 0 | 0 |
| 21-27 | -0.07 | -21 | -57 | | | | 0 | 0 |
| 28-34 | -0.15 | -59 | -60 | | | | 0 | 0 |
| 35-41 | -0.08 | -57 | -48 | | 5.0 | 2.8 | 0 | 2.1 |
| 42-48 | -0.04 | -72 | -58 | -55 | | | 2.3 | 4.7 |
| 49-55 | -0.04 | '47 | | | 4.5 | 2.0 | | |
| 56-62 | -0.05 | -47 | -42 | | 3.8 | 1.4 | 2.9 | 5.7 |
| 63-71 | -0.01 | -32 | -41 | | 2.3 | 0.9 | 6.1 | 7.5 |

*All "% change" values show the mean percentage gain (+) or loss (−) in value of the treated animals compared to the untreated dystrophic controls. All values are the mean of the group.

TABLE II

| | | | EXPERIMENT 3 - IAPP - 70 mg/Kg | | | | | |
| --- | --- | --- | --- | --- | --- | --- | --- | --- |
| Day | *% Weight Change | % CPK Change | % PK Change | % AChE Change | FN Treated | FN Control | WA Treated | WA Control |
| 7-13 | 0 | | | | | | | |
| 14-20 | -2 | | | | 5 | 5 | 0 | 0 |
| 21-27 | -3 | -51 | -32 | | 5 | 4.8 | 0 | 0 |
| 28-34 | -9 | -53 | -65 | | 5 | 5 | 0 | 0 |

Experiment No. 4

IAPP Injected into 3-Day Old Normal and Dystrophic Chickens

All chickens were injected with 50 mg/Kg IAPP and weighed approximately every second or third day.

The results are outlined in Table III below:

A: Control-injected with PBS
B, C, D: Experimental-injected with 50 mg/Kg IAPP

TABLE III

| | WEIGHT IN GRAMS Experiment No. 4 | | | | | | | | | | |
| --- | --- | --- | --- | --- | --- | --- | --- | --- | --- | --- | --- |
| Day | 1 | 4 | 7 | 9 | 11 | 14 | 16 | 17 | 20 | 22 | 25 |
| Dystrophic 413 | | | | | | | | | | | |
| A | 38.8 | 42.9 | 51.7 | 50.8 | | | | | | | |
| B | 48.3 | 51.2 | 56.7 | 58.1 | | | | | | | |
| C | 36.9 | 44.4 | 49.9 | 45.2 | 53.2 | 77.4 | 90.5 | 104.8 | | | |
| D | 44.5 | 51.2 | 59.8 | 56.5 | 65.4 | 93.7 | 115.1 | — | 161.3 | 210.2 | 240.7 |
| Normal | | | | | | | | | | | |

TABLE III-continued

| | WEIGHT IN GRAMS Experiment No. 4 | | | | | | | | | | |
|---|---|---|---|---|---|---|---|---|---|---|---|
| Day | 1 | 4 | 7 | 9 | 11 | 14 | 16 | 17 | 20 | 22 | 25 |
| 412 | | | | | | | | | | | |
| A | 49.6 | 59.1 | 74.9 | 76.1 | | | | | | | |
| B | 51.3 | 55.8 | 67.6 | 68.1 | | | | | | | |
| C | 50.8 | 59.9 | 67.8 | 67.7 | 76.4 | 111.8 | 139.0 | 150.2 | | | |
| D | 52.6 | 60.5 | 67.7 | 67.7 | 76.6 | 112.8 | 139.6 | — | 191.5 | 246.4 | 273.4 |

RESULTS

1. Weight Gain

There did not appear to be a toxic side effect of the IAPP injected chickens.

2. Flip Test (25 flips)

Both the normal and dystrophic drug injected chickens were able to pass the flip test. The exception to 25 flips was that the 413D experimental animal on day 25 fatigued after 19 flips while the 412D did not fatigue. This may have been due to lack of daily injections.

3. Culture Experiments

Essentially, these experiments were divided into three subgroups, taken from the previous Table:

Subgroup A
413A, 413B, 412A, 412B: All were sacrificed after 4 injections and muscle explants placed in culture.

Subgroup B
413C, 412C: All were sacrificed after 8 injections and muscle explants were placed in culture.

Subgroup C
413D, 412D: All were sacrificed after 10 injections and muscle explants placed in culture.

4. Culture Conditions

All explants were placed in CMRL culture medium containing 5% horse serum, 15% fetal bovine serum and 1% antibiotics and allowed to grow for 5-7 days before being fixed and observed for the presence or absence of microtubules. No IAPP was added to the culture medium during the 5-7 days in culture.

5. Microtubule Results

| | % Full Complexes Microtubules |
|---|---|
| Subgroup A | |
| 413A dyst. | 31% |
| 413B dyst. + IAPP | 58% |
| 412A normal | 86% |
| 412B normal + IAPP | 73% |
| Subgroup B | |
| 413C dyst. + IAPP | 60% |
| 412C normal + IAPP | 76% |
| Subgroup C | |
| 413D dyst. + IAPP | 74% |
| 412D normal + IAPP | 80% |

Some dystrophic 413 chickens appeared normal after 28 days of dilantin injections but explants from these animals did not have their microtubule defect corrected. Therefore, the state of microtubule assembly in dystrophic cells may be useful as a marker of improvement with drug therapy.

Effect of IAPP on Normal and Dystrophic Explants in Cell Culture

In these experiments 2-week and 3-week normal and dystrophic chickens (that had no previous injections with IAPP) were sacrificed and skeletal and cardiac explants were placed in culture with 0.5 mg/ml IAPP added. The pooled results of these experiments are as follows:

| | % Full Complexes Microtubules |
|---|---|
| 412 normal controls | 75% |
| 413 dyst. skeletal controls | 23% |
| 413 dyst. skeletal + IAPP | 38% |
| 413 dyst. cardiac control | 36% |
| 413 dyst. cardiac + IAPP | 43% |

These results suggest that dystrophic cells in culture contain reduced staining of microtubules which then appears to normalize upon incubation in IAPP.

Effects of IAPP on Human Blood Cells in Culture

Human monocytes from patients with Duchenne's muscular dystrophy do not spread out (become as flat) as normal cells when cultured for 5-7 days. In the experiments adding IAPP to such cultures, the preliminary results were as follows:

| | % Flat Cells |
|---|---|
| Normal monocytes (six individuals) | 61.3% |
| Dystrophic monocytes (six individuals) | 36.2% |
| Carrier monocytes (six individuals) | 35.3% |
| Dystrophic monocytes + IAPP (six individuals) | 45.1% |
| Carrier monocytes + IAPP (six individuals) | 50.0% |
| Dystrophic monocyte + dibutryl c-GMP (one individual) | 52.0% |

Based on Example I, a minimum concentration of 40 mg/Kg was found effective. An upper limit would be that amount where undesirable side effects occur such as weight loss due to toxicity (Example II 70 mg/Kg).

EXAMPLE II

First results with IAPP indicated that the maximum effective dosage may not have been reached. Thus, therapy with IAPP was continued giving higher doses than had been previously used, intraperitoneally. Further, after cessation of one month's continuous injections, a study of the parameters for a further two months was undertaken. This would enable any latent toxicity effects due to the drug to become apparent and would further provide information on any possible longer term beneficial effects of the drug on the parameters measured. It would determine whether physical, biochemical and histological improvements can be maintained in the absence of the drug and, if so, for what period.

Again, the necessity for daily injections, as opposed to less frequent therapy, has obvious relevance to the clinical condition where the least number of occasions necessary for medication is a desirable aim. In order to test whether continuous daily therapy produced a better or equal effect than less frequent injections, a comparison of the effects of injections given three times weekly, with those obtained with daily injections was also undertaken.

Finally, oral therapy with IAPP was undertaken at gradually increasing dosages up to 1 g/Kg/day. The parameters (physical, biochemical and histological) measured previously were again used to test the efficacy of the drug; five different dosages were used orally, each being given for 30-60 days, daily (Tables VII-XI). A total of 75 animals were treated in the current study with IAPP and 70 control animals were used.

Daily, intra-peritoneal injections (I.P.) of IAPP at 200 mg/Kg for 28 days gave a large reduction in plasma enzume levels, but physical performance was not significantly improved (Table IV). Strikingly, however, a reduction in the plasma enzyme levels of creatinephosphokinase (CPK), pyruvate kinase (PK) and acetylcholinesterase (AChE) from control values was maintained for a further period of 56 days, after injections of the drug had ceased. The mean flip number (denoting the number of times the bird can rise from the supine out of 5 attempts) was also slightly improved. Weight loss (after 30 days' treatment) became significant at the twenty percent level.

A similar pattern was seen with I.P. injections of IAPP at 300 mg/Kg. Plasma enzyme activities were again greatly reduced, although the reduction was not maintained for the full period of a further eight weeks, after the first four weeks of treatment (Table V). A comparison of daily therapy, with that given three times weekly (Mon., Wed., and Fri.) at the same dosage of 300 mg/Kg, gave very comparable reductions in plasma enzyme levels, which were maintained at a reduced level for the 56 days after treatment ceased (Table VI). The significant difference between the two methods of therapy (continuous and intermittent) was shown in the amount of weight loss sustained. In the former case of daily therapy, weight loss reached 28% which is high; in the latter case of 3-day/week therapy, weight loss reached only 17% with what appeared to be a very similar therapeutic effect.

Higher I.P. dosages were not, therefore, given since toxicity at 300 mg/Kg (daily) had reached unacceptable levels (i.e. above 20%).

Oral therapy was started at 200 mg/Kg and continued for 60 days; it gave only a moderate reduction in plasma CPK levels, with no effect on the physical performance parameters tested. Toxicity was minimal at 3% (Table VII). Similar results were obtained at 300 and 450 mg/Kg (Tables VIII and IX). At 600 mg/Kg, it first became apparent that significant reductions in enzyme levels and improvements in physical performance could be obtained in oral therapy (Table X), whereas weight loss was still insigificant (4%). At a still higher dosage, 1 g/Kg (Table XI) daily the first four weeks of treatment showed a highly significant reduction in enzyme levels and the physical performance parameters were greatly improved. Fifty percent of the birds were able to rise from the supine position 5 times out of 5 attempts (equivalent to normal birds) compared to only 20% of the dystrophic controls. Wing apposition was also greatly improved.

In conclusion, an effective oral dosage has been reached at 1 g/Kg, which when given to the chicken daily for 35 days, showed both dramatic reductions in three different plasma enzyme levels, normally greatly elevated in chicken dystrophy, and also improvements in the physical performance parameters which are notoriously difficult to alter when the dystrophic symptoms become established. Histological studies correlated with these results, showing marked improvements in the muscle morphology. Very little toxicity was observed during oral therapy of IAPP, maximum weight loss showing a 7% reduction from control values.

Further, improvements in the biochemical parameters noted during high-dosage intra-peritoneal therapy were maintained for relatively long periods after therapy ceased. It is believed that this is the first time that this has been observed in the chemotherapy of muscular dystrophy.

The finding that less frequent injections of IAPP had a comparable effect to daily injections, is one that could profitable be further explored. The observation was made over a 30-day period of therapy and it is possible that as the dystrophic symptoms become more severe, the necessity for daily injections would be apparent.

Histopathology

Figure 1A:
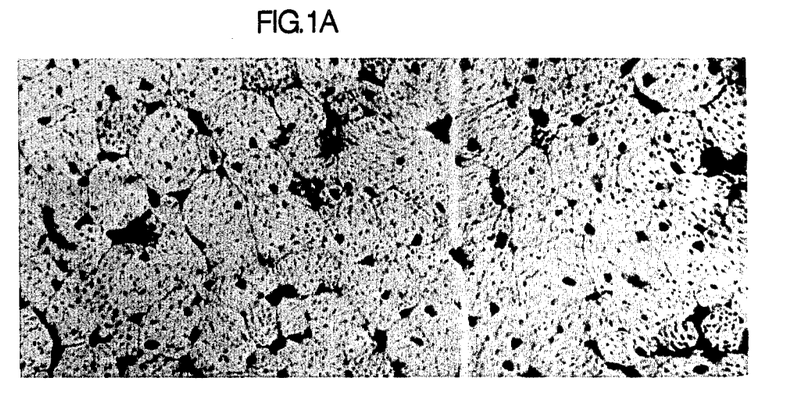
FIGS. 1(a)-1(c) illustrate the differences in fibre of normal muscle, dystrophic control and treated muscle, at four weeks.
Figure 2A:
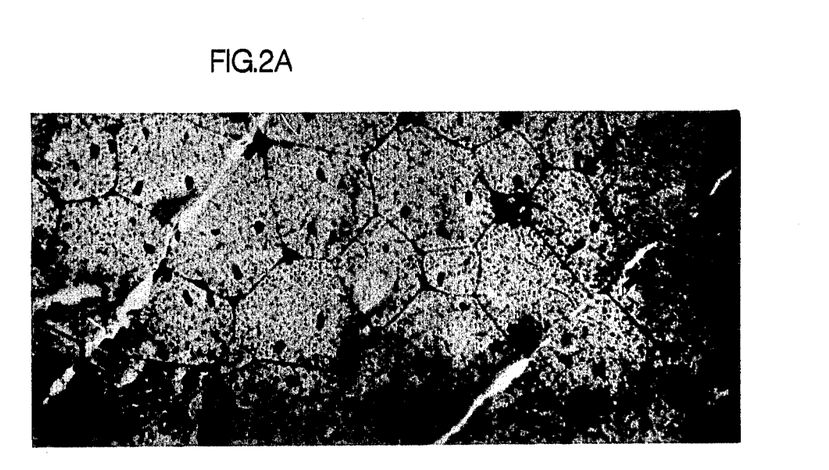
FIGS. 2(a)-(c) illustrate the difference in the fibre of normal muscle, dystrophic control and treated muscle at seven weeks.

The main difference between 4-week (FIG. 1A) and 7-week old (FIG. 2A) *normal* muscle from pectoral biopsies, at the light microscopic level, is with regard to myofibre growth. There is an increase in fibre area and a redistribution of the position and number of muscle nuclei. The latter change from a random distribution in the fibre in the 4-week bird to a central location in the 7-week bird of about 80% of the nuclei. The fibres are closely packed, with very little connective tissue present and every fibre is clearly polygonal in shape.

Figure 1B:
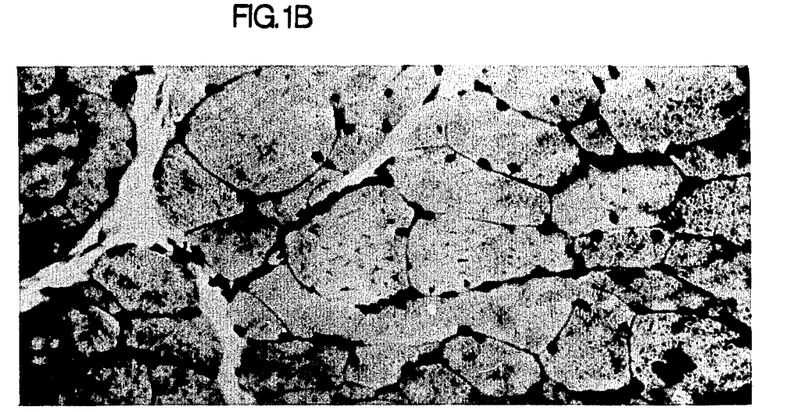
Figure 2B:
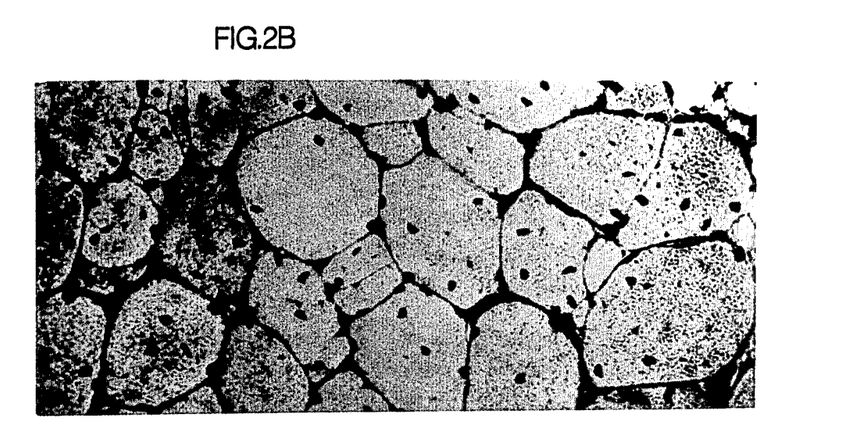

In contrast, dystrophic pectoral muscle has very few fibres which appear normal at 4 weeks of age. They are nearly all rounded in shape (as opposed to polygonal) and many are hypertrophic. Longitudinal fibre splitting occurs and the muscle nuclei lie preferentially against the sarcolemma (FIG. 1B). There is a large increase in perimysial connective tissue. By 7 weeks, massive hypertrophy occurs (FIG. 2B). Fibre splitting leads to hyperplasia. Necrosis, phagocytosis and cellular infiltration are greatly increased. Pyknotic nuclei appear, and the muscle nuclei are randomly scattered throughout the fibre. Connective tissue often appears very dense. Some fibres are starting to atrophy and fatty tissue replacement can sometimes be seen at this stage.

This rapid degeneration of the muscle fibre in the relatively short periof of seven weeks from hatching indicates what an extraordinary task is faced when improvement in fibre appearance is sought by chemotherapy. The condition of the dystrophic chicken at 7 weeks is now somewhat akin in deterioration to the 'wheelchair' human condition at 10-11 years of the Duchenne disease.

Figure 1C:
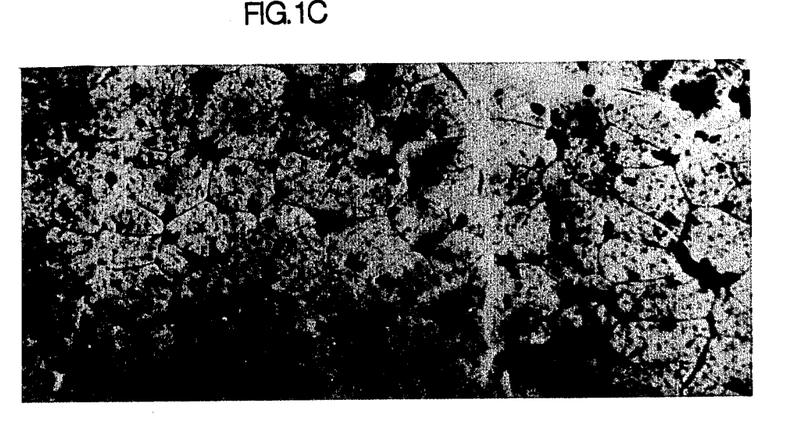

Muscle fibres from IAPP-treated bird (300 mg/Kg 3 times/week at 30 days) is shown in FIG. 1C. All fibres are polygonal, with nuclei numbers, distribution, fibre area range and connective tissue content all falling within the normal range. There is no sign of cellular reaction and the muscle is indistinguishable from normal muscle.

Figure 2C:
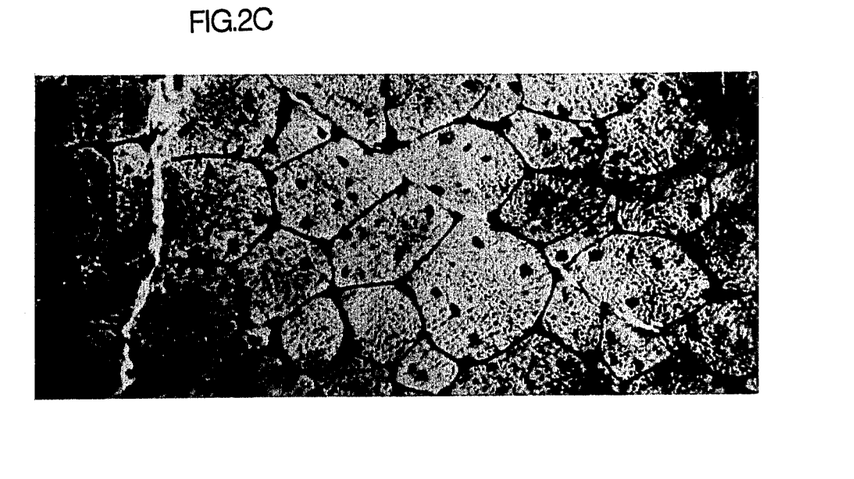
Figure 3:
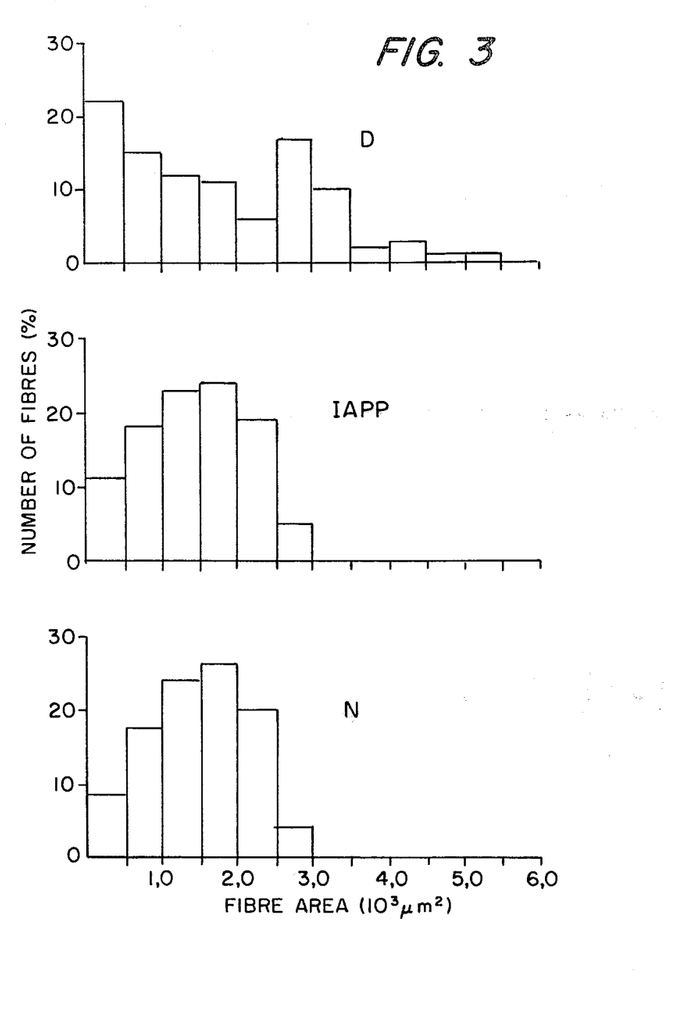
FIGS. 3-6 are histograms of fibre area and peripheral nuclei.
Figure 4:
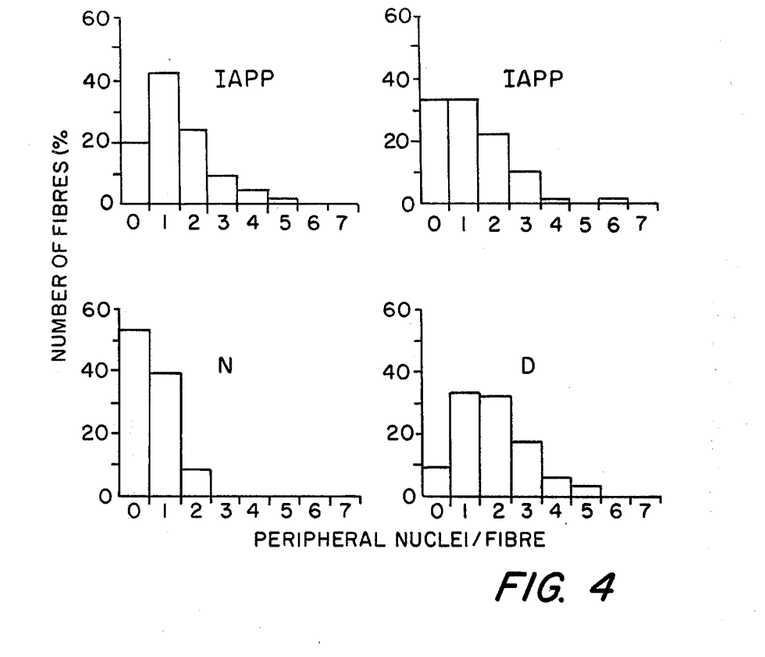
Figure 5:
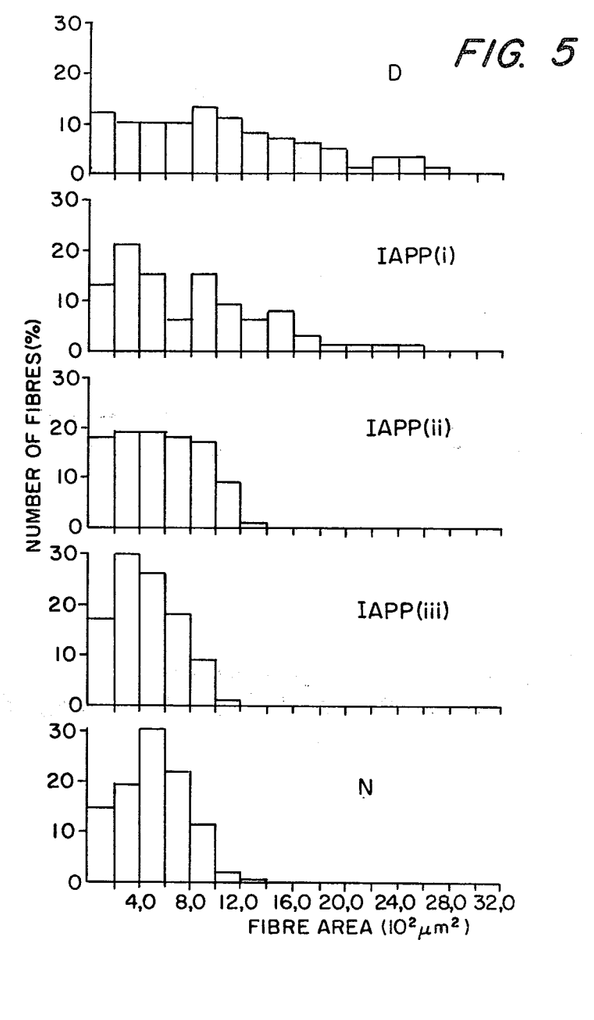
Figure 6:
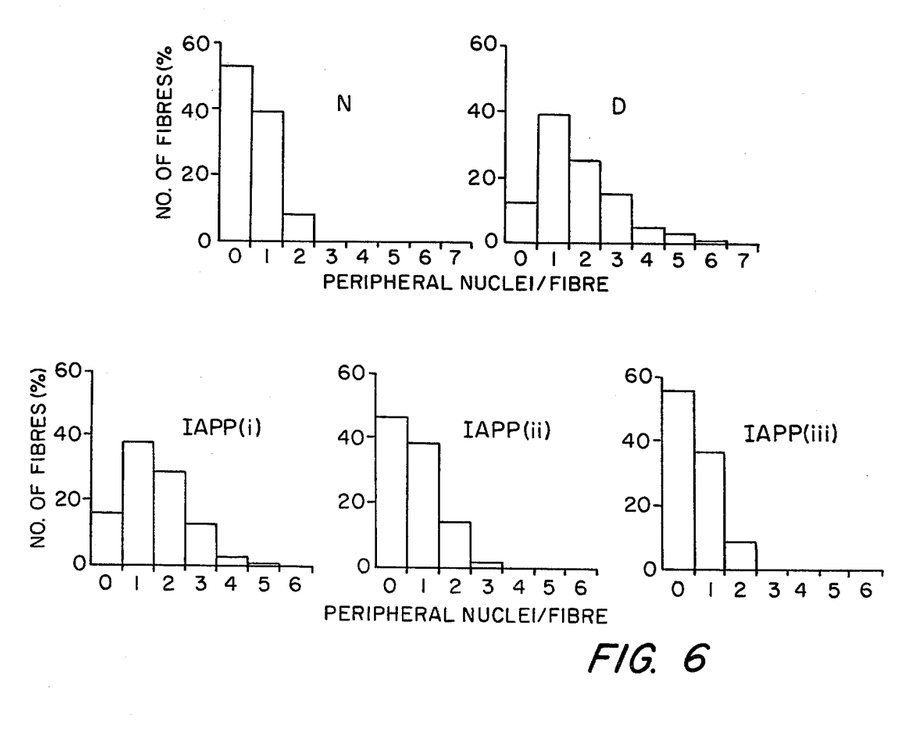

For comparison, a 7 week old muscle biopsy from an IAPP-treated bird (150 mg/Kg, daily) shows that 50% of the fibres are still polygonal although a few have become hypertrophic (FIG. 2C). There are areas of phagocytosis and degeneration; but the incidence is lower than in the dystrophic control. A few fibres are split and connective tissue involvement has increased slightly. Some fibres show granularity and others have nuclei fragmentation. There is less variation in fibre area than in the untreated bird and the size of fibres is generally smaller. Although the distribution of the nuclei is slightly normalised, the number per fibre is larger than normal.

Histological analysis over a range of dosages (Table XII) shows that the parameters measured most closely approximate the normal values when the dosage is at 300 mg/Kg (I.P.). Histograms of fibre area and peripheral nuclei further illustrate this point (FIGS. 3–6).

The histological data establishes significant improvement in muscle fibre morphology which can be correlated with the other parameters discussed above.

TABLE IV
EFFECT OF IAPP, INJECTED (I.P.) AT 200 mg/Kg, DAILY FOR 30 DAYS

| DAY ex ovo | CPK mU/ml | PK | AChE | FN T | FN C | WA T | WA C |
|---|---|---|---|---|---|---|---|
| 28 | 478 −61% | 377 −47% | | 5.0 | 4.9 | 1.0 | 0.4 |
| 45 | 4810 −40% | | 60.4 −29% | 3.3 | 3.5 | 1.5 | 0.6 |
| 56 | 5412 −48% | 1612 −45% | | | | | |
| 84 | 13,540 −36% | 2949 −36% | 87 −46% | 1.4 | 0.7 | 8.6 | 8.3 |

T IAPP-treated—10 animals
C Dyst. Control—10 animals
Maximum Weight Loss—19%

TABLE V
EFFECT OF IAPP, INJECTED (I.P.) AT 300 mg/Kg, DAILY FOR 30 DAYS

| DAY ex ovo | CPK mU/ml | PK | AChE | FN T | FN C | WA T | WA C |
|---|---|---|---|---|---|---|---|
| 28 | 651 −46% | 429 −40% | | 4.5 | 4.9 | 0.3 | 0.4 |
| 45 | 4505 −44% | | 48.4 −43% | 2.3 | 3.5 | 1.6 | 0.6 |
| 56 | 7629 −27% | 2447 −16% | | | | | |
| 84 | 24,248 +15% | 5282 +15% | | 0.1 | 0.7 | 14.4 | 9.3 |

T No. of TAPP-treated—10 animals
C Dyst. Controls—10 animals
Maximum Weight Loss—28%

TABLE VI
EFFECT OF IAPP, INJECTED (I.P.) AT 300 mg/Kg, FOR 30 DAYS, THREE TIMES WEEKLY

| DAY ex ovo | CPK mU/ml | PK | AChE | FN T | FN C | WA T | WA C |
|---|---|---|---|---|---|---|---|
| 28 | 651 −46% | 499 −30% | | 4.5 | 4.9 | 0.3 | 0.4 |
| 45 | 6076 −24% | | 62.9 −27% | 2.7 | 3.5 | 2.0 | 0.6 |
| 56 | 7944 | 2486 | | | | | |
| 84 | 16,602 −21% | 3766 −18% | 90 −45% | 0.6 | 0.7 | 11.1 | 8.3 |

T No. of Treated Animals—10
C No of Dyst. Controls—10
Maximum Weight Loss—17%

TABLE VII

| DAY ex ovo | CPK mU/ml | PK | AChE | FN T | FN C | WA T | WA C |
|---|---|---|---|---|---|---|---|
| 28 | 3496 −31% | 1925 −4% | | 4.1 | 5.0 | 0.8 | 0.8 |
| 35 | 7336 −1% | 2150 +6% | 77.8 −6% | 3.6 | 4.4 | 2.5 | 1.2 |
| 45 | 9638 −18% | | | 2.4 | 3.2 | 4.3 | 3.4 |
| 60 | 10,860 −24% | | | 1.8 | 2.8 | 10.7 | 9.6 |

T No. of Treated Animals—10C No. of Dyst. Controls—10
Maximum Weight Loss—3%

TABLE VIII
EFFECT OF IAPP, ORAL INJECTIONS AT 300 mg/Kg, DAILY

| DAY ex ovo | CPK mU/ml | PK | AChE | FN T | FN C | WA T | WA C |
|---|---|---|---|---|---|---|---|
| 28 | 3794 −23% | 2010 +1% | | 4.7 | 4.8 | 1.4 | 1.6 |
| 35 | 6690 −30% | 907 +28% | | 4.4 | 4.7 | 4.5 | 1.3 |

T No. of Treated Animals—7
C No. of Dyst. Controls—10
Maximum Weight Loss—10%

TABLE IX
EFFECT OF IAPP, ORAL INJECTIONS AT 450 mg/Kg, DAILY FOR 45 DAYS

| DAY ex ovo | CPK mU/ml | PK | AChE | FN T | FN C | WA T | WA C |
|---|---|---|---|---|---|---|---|
| 28 | 4713 −18% | | 520 −12% | 5.0 | 5.0 | 0.7 | 0.2 |
| 35 | 6483 −24% | 2520 +0.6% | | 4.8 | 3.6 | 1.9 | 2.8 |
| 45 | | | | 2 | 1.7 | 5.8 | 5.5 |
| 50 | 17,975 +30% | 3891 +7% | | 1 | 1.4 | 7.6 | 6.2 |

T No. of Treated Animals—9
C No. of Dyst. Controls—10
Maximum Weight Loss—3%

TABLE X
EFFECT OF IAPP, ORAL INJECTIONS, DAILY AT 600 mg/Kg

| DAY ex ovo | CPK mU/ml | PK | AChE | FN T | FN C | WA T | WA C |
|---|---|---|---|---|---|---|---|
| 28 | 2658 −53% | | 46.9 −21% | 5.0 | 5.0 | 0.3 | 0.2 |
| 35 | 4712 −45% | 1639 −36% | | 4.3 | 3.6 | 1.1 | 2.8 |
| 45 | | | | 2.7 | 1.7 | 3.5 | 5.5 |
| 50 | 9084 −34% | 2824 −22% | | 2.3 | 1.4 | 5.5 | 6.2 |

T No. of Treated Animals—9
C No. of Dyst. Controls—10
Maximum Weight Loss—4%

TABLE XI
EFFECT OF IAPP, ORAL INJECTIONS AT 1 g/Kg, DAILY

| DAY ex ovo | CPK mU/ml | PK | AChE | FN T | FN C | WA T | WA C |
|---|---|---|---|---|---|---|---|
| 28 | 2217 −63% | 1080 −48% | | 3.5 | 1.7 | 0.8 | 1.8 |
| 35 | 4018 −68% | 1812 −50% | 53.9 −47% | | | | |

T No. of Treated Animals—10
C No. of Dyst. Controls—10
Maximum Weight Loss—3%

TABLE XII
HISTOLOGICAL ANALYSIS OF IAPP-TREATED BIRDS AT 30 DAYS

| Dosage | 10 (NORH) | 150 mg | 200 mg | 300 mg | 300 mg (3× wk.) | (DYS/CON) |
|---|---|---|---|---|---|---|
| Mean Endomysial Area ($\mu m^2$) | 504 | 1025 | 763 | 552 | 449 | 997 |
| S.D. | 237 | 426 | 541 | 320 | 233 | 652 |
| Range ($\mu m^2$) | 30–1217 | 82–2001 | 54–2554 | 24–1226 | 51–1060 | 68–2767 |
| Variability Coefficient | 470 | 416 | 709 | 580 | 518 | 654 |
| Hypertrophy Factor | 25 | 125 | 460 | 100 | 10 | 770 |
| % Phagocytosis | 0.0 | 0.0 | 1.6 | 0.3 | 0.0 | 0.3 |
| % Fibre Splitting | 3.0 | 3.0 | 8.4 | 10.3 | 3.0 | 12.4 |
| Nuclei/Fibre | 1.5 | 2.5 | 2.5 | 1.7 | 1.3 | 2.3 |
| Peripheral Nuclei (% of Total) | 43.1 | 46.1 | 59.1 | 42.1 | 40.9 | 77.8 |

The disclosed compound is applicable for the treatment of physiological disorders directly or indirectly linked to the muscular neurotransmission; this would include myopathy of endocrine origin, myotonia and muscular dystrophy, including inherited (with and without myopathy) and acquired (toxic, infectious, immunological or from dietary origin).

The preferred embodiment of the invention has been described in reference to a therapeutically acceptable salt of a substituted 2-aminopyrimidine. The following salts derived from a substituted 2-aminopyrimidine are also considered within the scope of the invention.

TABLE XIII

| Name | Solvent (l) | Melting Point | Formula |
|---|---|---|---|
| methane sulfonate | E/A | 92° | $C_8H_{15}N_3O_3S$ |
| p-toluene sulfonate | E | 155° | $C_{14}H_{19}N_3O_3S$ |
| camphosulfonate | E | 130° | $C_{17}H_{27}N_3O_4S$ |
| succinate | E/A | 134° | $C_{11}H_{17}N_3O_4$ |
| fumarate | E/A | 230° | $C_{11}H_{15}N_3O_4$ |
| maleate | E/A | 73° | $C_{11}H_{15}N_3O_4$ |
| bromo furoate | E | — | $C_{12}H_{14}BrN_3O_3$ |
| nitrofuroate | E | 112° | $C_{12}H_{14}N_4O_5$ |
| nicotinate | E/A | 220° | $C_{13}H_{16}N_4O_2$ |
| benzoate | E | — | $C_{14}H_{17}N_3O_2$ |
| cyclohexane carboxylate | E | — | $C_{14}H_{23}N_3O_2$ |
| phenyl acetate | E | — | $C_{15}H_{19}N_3O_2$ |
| cinnamate | E | — | $C_{16}H_{19}N_3O_2$ |
| aspartate | water | >260° | $C_{11}H_{18}N_4O_4$ |
| anthranilate | A | 62° | $C_{14}H_{18}N_4O_2$ |
| amino-4-phenylacetate | A | 208° | $C_{15}H_{20}N_4O_2$ |
| inosinate | water | 210° | — |
| orthophosphate diacide | E/A | 120° | $C_7H_{14}N_3O_4P$ |
| D-tartrate | MeOH | 110° | $C_{11}H_{17}N_3O_6$ |
| theophylline acetate | water/EtOH | >260° | $C_{16}H_{21}N_7O_4$ |

A = ethyl alcohol
E = ethyl ether

It is possible that the salt used, IAPP, may be metabolized when absorbed in the host system under examination. The IAPP may be either hydroxylated or oxydated and the following formulaes are believed to represent possible metabolites:

hydroxylated

A specific salt of a substituted 2-aminopyrimidine $C_4H_5N_3$ has been disclosed. Other pyrimidine compounds, their salts and metabolites may be used, such as 2-amino and 4-aminopyrimidine; $C_4H_5N_3O_2$ (2-amino-4, 6-dihydroxpyrimidine; 6-amino-2, 4-dihydroxypyrimidine); $C_6H_9N_3$ (2-amino-4, 5-dimethylpyrimidine and 4-amino-2, 6-dimethylpyrimidine and 6-amino-4, 5-dimethylpyrimidine); $C_5H_7N_3$ (2-amino-4-methylpyrimidine, 2-amino-5-5-methylpyrimidine, 4-amino-2-methylpyrimidine, 4-amino-5-methylpyrimidine and 6-amino-4-methylpyrimidine); $C_4H_4N_4O_2$ (2-amino-5-nitropyrimidine); $C_9H_{14}ClN_3$ (2-chloro-4-(diethylamino)-6-methylpyrimidine); $C_5H_4Cl_2N_2$ (2, 4-dicholor-5-methylpyrimidine, 2, 4-dicholor-6-methylpyrimidine); $C_4H_4N_2O.HCl$ (2-hydroxy pyrimidinehydrochloride); $C_5H_6N_2$ (2 methylpyrimidine); $C_5H_7N_3$ 4-(methylamino)pyrimidine; uracil and cytosine.

Having described my invention, what I now claim is:

1. A method for the chemotherapy of muscular dystrophy, myopathy, and myotonia which comprises:
   administering to an animal afflicted with a condition associated with muscular dystrophy, myopathy or myotonia 2-isopropylanimopyrimidine or therapeutically acceptable salts of the same in an amount effective to improve said condition.

2. The method of claim 1 wherein the animal is a human.

3. The method of claims 1 or 2 wherein one therapeutically acceptable salt is 2 isopropylaminopyrimidine orthophosphate.

4. The method of claim 3 wherein the condition is muscular dystrophy.

5. The method of claim 3 wherein the administering includes oral administration.

* * * * *